United States Patent
Magness et al.

(10) Patent No.: US 7,041,455 B2
(45) Date of Patent: May 9, 2006

(54) METHOD AND APPARATUS FOR PATTERN IDENTIFICATION IN DIPLOID DNA SEQUENCE DATA

(75) Inventors: Charles Lee Magness, Seattle, WA (US); Dake Sun, Redmond, WA (US)

(73) Assignee: Illumigen Biosciences, Inc., Seattle, WA (US)

( * ) Notice: Subject to any disclaimer, the term of this patent is extended or adjusted under 35 U.S.C. 154(b) by 0 days.

(21) Appl. No.: 10/383,922

(22) Filed: Mar. 7, 2003

(65) Prior Publication Data

US 2004/0175702 A1 Sep. 9, 2004

(51) Int. Cl.
*C12Q 1/68* (2006.01)

(52) U.S. Cl. ............................................. 435/6; 702/20
(58) Field of Classification Search .................. 702/19, 702/20; 435/6
See application file for complete search history.

(56) References Cited

OTHER PUBLICATIONS

Daly et al, Nature Genet. 29: 229 (2001).*
Martinez-Arias et al, DNA Sequence 13: 9 (2002).*
Benton, TIBTECH 14: 261 (1996).*

* cited by examiner

*Primary Examiner*—James Martinell
(74) *Attorney, Agent, or Firm*—Michael J. Donohue; Davis Wright Tremaine LLP

(57) ABSTRACT

This invention provides methods for identifying mutations and methylation patterns in diploid DNA sequence signal data. In particular, the invention provides methods for (1) obtaining two parental allele sequences from diploid DNA sequence signal data, (2) identifying the mutation and haplotype patterns in the two parental allele sequences, (3) assigning likelihood scores for the mutations thus identified, and (4) identifying patterns of methylation.

65 Claims, 6 Drawing Sheets

An example of a diploid DNA sequence signal, where the bases in the parenthesis show overlapping peaks:
ACG(G/T)CGGCC Two initial base sequences are as follows:
ACGGCGGCC
ACGTCGGCC

*Fig. 5*

Two initial base sequences:
ACGGCGGCC
ACGTCGGCC

A swap of G and T in the fourth position:
ACGTCGGCC
ACGGCGGCC

*Fig. 6*

METHOD AND APPARATUS FOR PATTERN IDENTIFICATION IN DIPLOID DNA SEQUENCE DATA

STATEMENT REGARDING FEDERALLY SPONSORED RESEARCH OR DEVELOPMENT

This invention was made with government support under NIH Grant No. CA90095 awarded by National Institutes of Health.

BACKGROUND OF THE INVENTION

1. Field of the Invention

The present invention is directed generally to genetic and genomic analysis and more particularly to methods for identifying mutations and methylation patterns in diploid DNA sequence data.

2. Description of the Related Art

Genetic Variation

It is well known that certain genetic variations (also called genetic mutations or polymorphisms) can result in disease susceptibility or differential drug response in individuals. It is of great interest to identify those genetic variations in disease and drug research.

In a diploid species, each individual has two copies of each gene. These may be derived from parental genes with one being a maternal copy and the other a paternal copy. The two copies are also known as alleles. A challenging problem is to identify the two sets of genetic variation that are on the two respective alleles for gametic phase unknown DNA sequence data.

There are two common approaches to the problem. One approach is to use molecular methods to separate the two alleles and identify the genetic variation on each separately. Such methods include Single Molecule Dilution (SMD), Allele-Specific polymerase chain reaction (PCR), and several cloning approaches. The molecular methods, however, are complex and expensive. They do not appear to be practical for regular, large-scale test under current technology. Another approach is to use computational methods to resolve the ambiguity in genetic variances assignment and derive the true alleles from data that is composed of a mixture of the two alleles.

DNA Methylation

With regard to DNA methylation it has been known that methylation of cytosine-rich regions of DNA is involved in gene silencing. Differential methylation was found to be a key element in the transcription regulation of genes. Experiments have shown that methylation of the so-called CpG island of a gene inhibits transcription. It is believed that methylation either directly inhibits the binding of transcription factors or methylcytosine-binding proteins interact with other structural compounds, therefore making the DNA inaccessible to transcription factors. Methylation status has been shown to be associated with disease. For example, the development of certain cancers in mammalia was found to be accompanied by genome wide demethylation and local hypermethylation of tumor suppressor genes. As a result, it is of great interest to obtain the methylation pattern in DNA, in addition to the genetic variation in studying disease susceptibility and associated treatments.

After the introduction of the Bisulfite Genomic Sequencing technique, it has become possible to study small amounts of DNA and to identify methylation patterns with single base resolution. This technique selectively deaminates unmethylated cytosine to uracil in the DNA strand by treatment of the DNA with a solution of sodium bisulfite. PCR amplification of such bisulfite-treated DNA replicates the uracils as thymines. After PCR, methylation patterns can be identified by a comparison of the PCR amplified sequence with the original sequence. As used herein, bisulfite-treated DNA refers to DNA that has been treated with a bisulfite solution and PCR amplified to replace all unmethylated cytosines with thymines.

Methylation identification can be readily solved by the technique if the gametic phase is known for the underlying DNA sequence data. However, commonly available sequence data usually has two confounding characteristics: (1) the gametic phase is unknown (i.e., each allele can not be assigned to a particular parent), and (2) the data contains underlying genetic variation (e.g., insertion or deletion of specific nucleotide bases relative to a reference sequence). For such data, applying the Bisulfite Genomic Sequencing technique alone may not be able to resolve actual methylation patterns. Solutions are needed which can resolve unknown phase sequence data and account for the underlying genetic variation in identifying methylation patterns.

Therefore, it can be appreciated that there is a significant need for techniques to identify gametic phase and genetic mutations. The present invention provides this and other advantages as will be apparent from the following detailed description and the accompanying figures.

BRIEF SUMMARY OF THE INVENTION

The present invention is concerned with genetic mutation identification and methylation pattern identification in diploid DNA sequence signal data. More specifically, the invention relates to obtaining two parental alleles from diploid DNA sequence signal data, identifying genetic mutations, and/or identifying the methylation pattern in each parental allele. It is further concerned with assigning likelihood scores to the genetic mutations thus identified.

A method is disclosed for deriving two haploid DNA sequences from a diploid DNA sequence signal. A method is disclosed for identifying methylation patterns in a bisulfite-treated, diploid DNA sequence signal relative to two reference haploid DNA sequences. A method is disclosed for assigning a likelihood score to each of the genetic mutations identified on DNA sequences.

BRIEF DESCRIPTION OF THE SEVERAL VIEWS OF THE DRAWING(S)

FIG. 5 illustrates an example of generating initial base sequences generated from a diploid DNA sequence signal.

FIG. 6 shows a swapping of two bases in the initial base sequences, which is a step in the mutation identification process.

DETAILED DESCRIPTION OF THE INVENTION

The present invention describes analytical techniques by which a diploid DNA sequence may be parsed and analyzed to generate two haploid DNA sequences to permit the identification of the gametic phase. Further, the techniques described herein can be used to identify genetic mutations.

Figure 1:
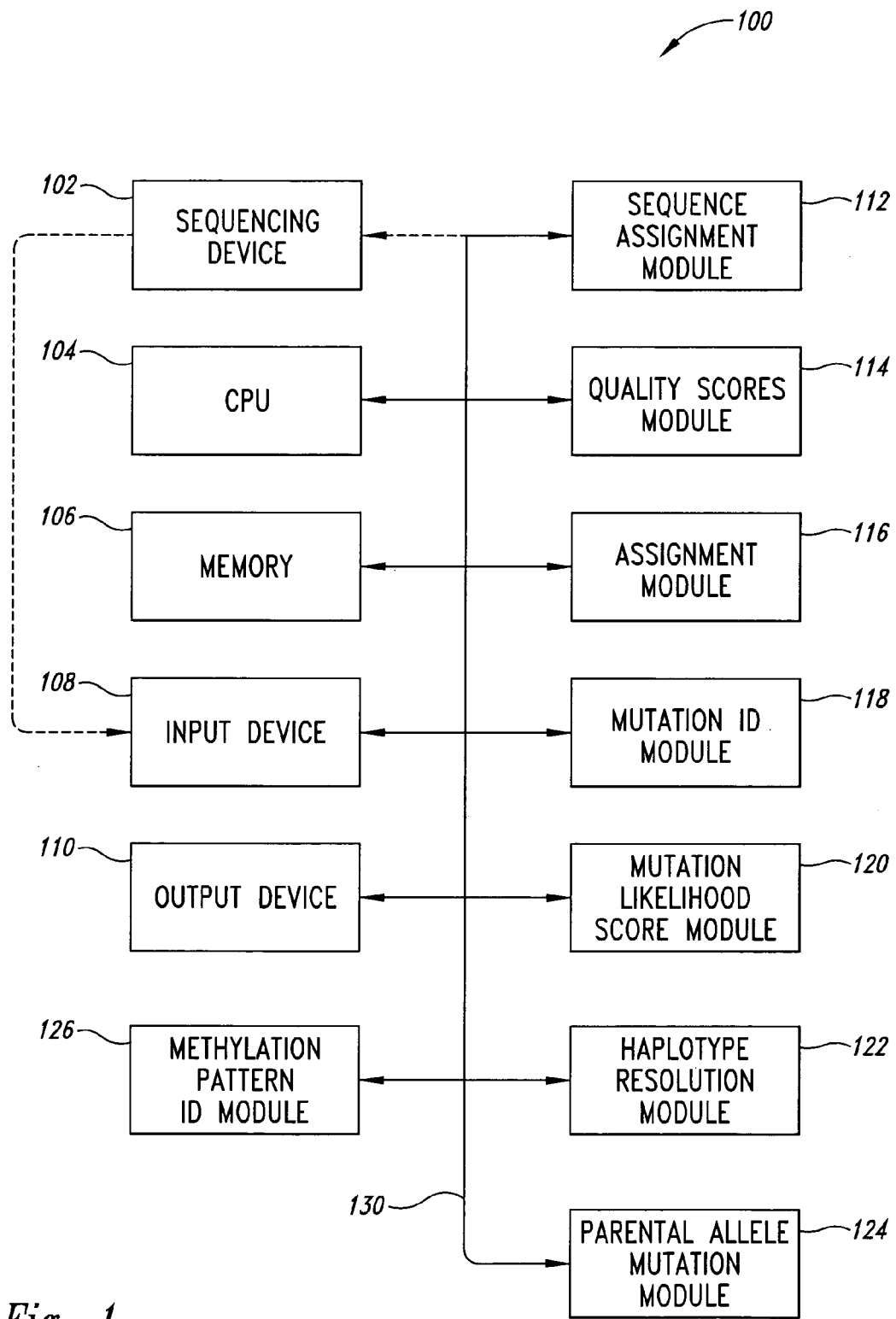
FIG. 1 is a functional block diagram of a system capable of implementing the techniques described herein.

FIG. 1 is a functional block diagram of a system 100 constructed in accordance with the teachings contained herein. The system 100 includes a sequencing device 102 to generate a diploid DNA sequence signal. The system 100 is not limited by the specific implementation of the sequencing device 102. In one embodiment, the sequencing device 102 may be an electrophoresis sequencing device, as is known to those skilled in the art. However, the system 100 may be operated satisfactorily with other sequencing devices that generate electrical signals indicative of the sequence of DNA bases. The sequencing device 102 is coupled to a computer. The coupling of the sequencing device 102 to the computer may be implemented by a number of interfaces including input devices 108 or bus system 130 (each described further below).

The computer includes a central processing unit (CPU) 104 and a memory 106. The CPU 104 may be implemented by a number of known devices, such as microprocessors, microcontrollers, digital signal processors, or the like. The system 100 is not limited by the specific device used to implement the CPU 104. Similarly, the memory 106 is implemented using known technology. The memory 106 may comprise read-only memory, random-access memory (RAM), flash memory and the like. The system 100 is not limited by the specific implementation of the memory 106. The memory 106 contains data and instructions for execution by the CPU 104.

The system 100 also includes input devices 108, such as a keyboard, a mouse, a serial input interface, such as a universal serial bus (USB) interface, and the like. For the sake of brevity, the various input devices are illustrated in FIG. 1 as the input devices 108. FIG. 1 also illustrates generic output devices 110. Output devices may include, but are not limited to, audio and video output devices, printers, and the like. Again, for the sake of brevity, output devices are not individually illustrated, but are shown in FIG. 1 as the output devices 110.

A sequence assignment module 112 splits a diploid DNA sequence signal obtained through the sequencing device 102 into two base sequences that are the first guess of the two parental alleles and to be improved by an alignment module 116.

A quality score module 114 assigns quality scores for each base in the two parental alleles obtained by the sequence assignment module 112.

The alignment module 116 improves the initial two parental alleles obtained by the sequence assignment 112 and determines the final form of the two parental alleles.

A mutation identification (ID) module 118 identifies the mutations in the two parental alleles obtained by the alignment module 116.

A haplotype resolution module 122 resolves the haplotypes for the mutations identified by the mutation ID module 118.

A mutation likelihood score module 120 assigns likelihood scores to the mutations identified by the mutation ID module 118 based on the quality scores obtained by the quality score module 114.

A parental allele mutation module 124 combines the results of modules 118, 120 and 122 and shows the mutation haplotypes with likelihood scores.

A Methylation Pattern ID module 126 identifies the methylation patterns presented in the parental alleles.

Operational details of these modules are provided below. Those skilled in the art will appreciate that many of the blocks described above may be implemented by hardware components or by software components. For example, many of the modules, such as the alignment module 116, mutation ID module 118, and mutation likelihood score module 120, may be implemented by a set of computer instructions stored in the memory 106 and executed by the CPU 104. However, each of these components is illustrated as separate functional blocks in the block diagram of FIG. 1 since each performs a separate function.

The various components illustrated in FIG. 1 are coupled together by a bus system 130. The bus system 130 may comprise an address bus, data bus, power bus, control bus, and the like. However, for the sake of simplicity, the various buses are illustrated in FIG. 1 as the bus system 130.

Methods Overview

The identification of genetic mutations and/or methylation patterns in genes that may be involved in disease susceptibility, disease resistance or drug response are useful for determining whether the genetic mutations and/or methylation patterns account for the disease susceptibility, resistance and drug response and for determining whether a given disease susceptibility, disease resistance or drug response has a genetic basis. The identification of genetic mutations and/or methylation patterns in genes further provides utilities for identifying drug targets and for predicting differences in response to treatment and selection of an appropriate treatment for a disease or condition.

The term "diploid DNA sequence signal data" as used herein refers to the data that is the output data generated by an electrophoresis sequencing device conducting a sequencing operation. In diploid organisms, there are two parental DNA alleles known as haplotypes for every corresponding location (or "locus") on each of the two chromosomes. The diploid DNA sequence signal data contains a mixture of the two haplotypes (i.e., the gametic-phase is unknown for some bases in the haplotype pair).

As can be appreciated by those skilled in the art, DNA sequence signal data is typically interpreted and thereafter represented as a series of alphabetic characters that denote the constituent nucleotide bases. The common naturally occurring nucleotides adenine, cytosine, guanine, and thymine are often represented by A, C, G, and T, respectively. The current invention is not limited, however, by the form, number, or representation of constituent DNA nucleotides. The current invention is also not limited by the presence of synthetic or other naturally occurring nucleotides in addition to those mentioned above. The representation of constituent nucleotides may alternately be referred to as nucleotide(s) or base(s) herein.

The current invention provides methods for (1) obtaining the two parental DNA alleles from the diploid DNA sequence signal data, (2) identifying genetic mutations or polymorphisms in each of the two parental DNA alleles, (3) assigning likelihood score to each genetic mutation in the two parental DNA alleles, and (4) identifying methylation patterns in each of the two parental DNA alleles, In a first aspect, the current invention provides a method for separating two parental DNA alleles from the diploid DNA sequence signal data by updating two initial alleles in comparison with a reference sequence. The current invention further improves the two parental DNA alleles obtained through the application of a haplotyping method.

In some embodiments of this invention, the haplotyping method is based on an expectation maximization algorithm to identify the haplotypes that are statistically most likely to account for the observed genetic variation. The haplotyping method utilizes a plurality of the parental DNA alleles that are to be improved.

Mutations occur in the human genome at approximately one in every 500–1,000 bases within the human genome when two alleles are compared. When multiple alleles from unrelated individuals are compared, the density of variant sites increases since different individuals, when compared to a reference sequence, will often have sequence variation at different sites. At most variant sites there are only two alternative nucleotides involving the substitution of one base for another or the insertion/deletion of one or more nucleotides. Within a gene there may be several variant sites. Variant forms of the gene or alternative alleles can be distinguished by the presence of alternative variances at a single variant site, or a combination of several different variances at different sites.

In another aspect, the current invention provides a method for identifying the genetic mutations or polymorphisms in each of the two parental DNA alleles.

In some embodiments of this invention, the genetic mutations or polymorphisms are identified by aligning the parental DNA alleles with a reference sequence using a dynamic programming algorithm. Both parental DNA alleles and the reference sequence are derived from the same locus.

The terms "genetic mutations" and "polymorphisms" as used herein refer to genetic variations that may include the substitution of base(s) for another or the insertion/deletion of one or more bases.

In yet another aspect, the current invention provides a method for assigning likelihood score to each genetic mutation in a parental DNA allele pair.

In some embodiments of this invention, the method for calculating likelihood score comprises calculating the quality score for each base using spacing parity and amplitude parity of the signal peaks in the diploid DNA sequence signal. The method for calculating likelihood score of a mutation further comprises using the weighted average value of quality scores for bases in the neighborhood of the mutation.

The term "methylation pattern" as used herein refers to the set of methylated cytosine in the DNA on a parental DNA allele.

In yet another aspect, the current invention provides a method for resolving the unknown phase and genetic mutations and identifying the methylation pattern in each of the two parental DNA alleles obtained using the methods developed in this invention.

In some embodiments of this invention, the methylation pattern is identified by aligning the parental DNA alleles with corresponding bisulfite treated parental DNA alleles using heuristic search and a dynamic programming algorithm. Both the parental DNA alleles and the bisulfite treated parental DNA alleles are derived from the same genomic locus.

Figure 2:
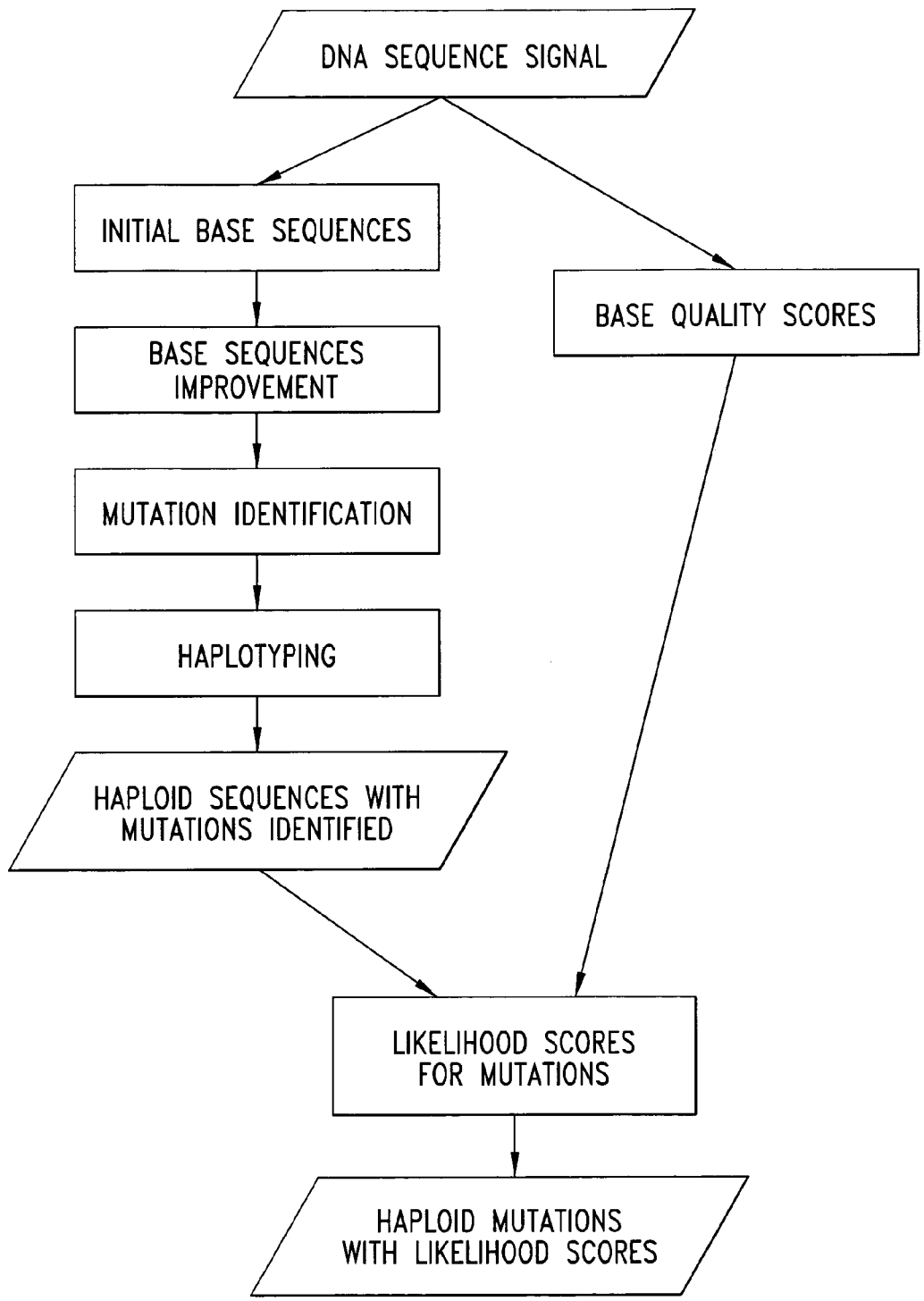
FIG. 2 illustrates one embodiment of an algorithm that enables the mutation identification process.

A set of methods is developed for genetic mutation identification in the present invention. The steps of the mutation identification process are shown in FIG. 2. The descriptions of the steps are given below.

Base Quality Scores (Quality Scores Module 114)

Quality scores for the bases are the basis for calculating the likelihood score of genetic mutations or polymorphisms in parental DNA sequences.

The quality scores for the bases are calculated based on spacing parity and amplitude parity of the signal peaks in the diploid DNA sequence signal. The spacing parity of a base is a measure of the discrepancy among the distances between two adjacent signal peaks in the neighborhood of the base in a diploid DNA sequence signal. The amplitude parity of a base is a measure of the discrepancy among the amplitudes of the signal peaks in the neighborhood of the base in the diploid DNA sequence signal.

In the following description about base quality score calculation, only quality scores for bases in base sequence 1 will be given. By the symmetry of the two base sequences, the quality scores for bases in base sequence 2 are calculated in the same fashion as those in base sequence 1 are calculated.

The spacing parity is calculated as the ratio of the largest distance between two adjacent peaks to the smallest distance between two adjacent peaks (excluding the distance between overlapping peaks) in a window of a given number of peaks (e.g., three or seven) in the diploid DNA sequence signal. The peaks include all peaks in both the base sequence 1 and base sequence 2.

The amplitude parity is calculated as the ratio of the largest peak amplitude between to the smallest peak amplitude in a window of a given number of peaks (e.g., three or seven) in the diploid DNA sequence signal. The peaks include all peaks in both the base sequence 1 and base sequence 2.

After the spacing parity and amplitude parity are calculated for all bases, the quality scores for the bases are obtained by looking up a quality score table using the spacing parity and said amplitude parity as the search key. The quality score table is a table that associates spacing parity and amplitude parity to a corresponding quality score (for detailed description of the quality score table, see [Ewing and Green, 1998].) The table may be a portion of the memory 106 (see FIG. 1) or a separate data storage area.

The base quality scores obtained by the above method will be used as the basis for calculating the likelihood scores for genetic mutations. The likelihood scores calculation will be described after the description of the haplotyping method.

Initial Base Sequences (Sequence Assignment Module 112)

Figure 4:
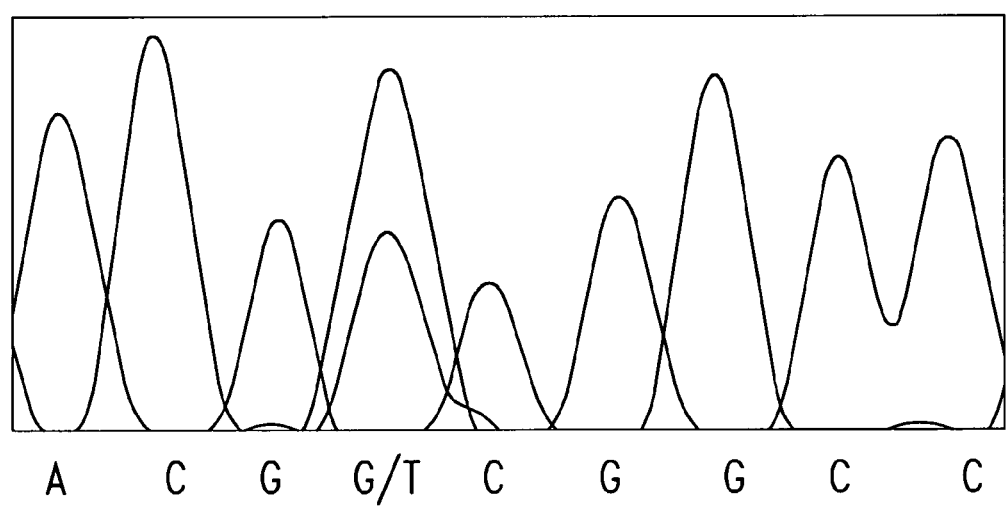
FIG. 4 illustrates an example of two overlapping peaks, G and T, in a diploid DNA sequence signal.

The diploid DNA sequence signal (illustrated in FIG. 4) is first decomposed into two constituent initial base signal sequences as shown in FIG. 5. The decomposition process first uses a threshold to filter out small signal peaks and noises at each signal peak position such that there are at most two signal peaks left at each position in the diploid DNA sequence signal. For example, for the sequence signal shown in FIG. 4, only the overlapping peaks G/T remain after the filtering. The decomposition process assigns the overlapped or partial overlapped signal peaks to different initial base signal sequences. If there is only one signal peak at a position, the peak is assigned to both initial base signal sequences.

In the following description, denote the two initial base signal sequences as base sequence 1 and base sequence 2, respectively. Each base in the base sequences corresponds to a signal peak in the diploid DNA sequence signal.

Base Sequence Improvement (Alignment Module 116)

The diploid DNA sequence signal is first decomposed into two base sequences. Because the bases in the diploid DNA sequence signal are phase unknown, the initial decomposition or base assignment may contain errors. That is, some bases may be assigned to the incorrect base sequence. The base assignment could be incorrect due to two types of mutations: (1) base substitution and (2) base insertion/deletion. In case of base substitution, two overlapping peaks will show up at a position in the diploid DNA sequence signal and there is not enough information for telling which corresponding base should be assigned to which base sequence. In case of base insertion/deletion, there could be many overlapping peaks after the mutation and for each pair of overlapping peaks and there is not enough information for telling which corresponding base should be assigned to which base sequence. In that case, significant portion of bases after the mutation could be assigned to the incorrect base sequence. Some embodiments of this invention provide methods to recover the two actual parental DNA base sequences from the initially incorrect base assignment.

The current invention provides two methods for correcting base assignment errors: (1) a method that improves the base sequences by correcting base assignment errors caused by insertion/deletion mutations, and (2) a method that improves the base sequences by correcting base assignment errors caused by base substitution mutations.

After initial decomposition or base assignment, there are two base sequences, denoted as base sequence 1 and base sequence 2. Assume that the base sequences contain incorrect bases due to the base insertion/deletion mutations described above. As a result, the genetic mutations will not be correctly identified if such base sequences are directly compared with a reference sequence.

One embodiment of a method is described below that can identify and correct the base assignment errors caused by the base insertion/deletion mutations in the base sequences. After the correction, the method aligns the corrected base sequences to a reference sequence to identify the mutations. The method is based upon the following observations: (1) the number of mutations in the base sequences is small so that the base sequences should match the reference sequence relatively well, and (2) the best match between each of the base sequences and the reference sequence is achieved when incorrect base assignments caused by base insertion/deletion mutations are corrected.

In one embodiment, the problem of correcting base assignments is constructed as the following optimization problem.

Denote the base sequence 1 as $S1=\{a_1, a_2, \ldots, a_n\}$ and the base sequence 2 as $S2=\{b_1, b_2, \ldots, b_n\}$ and a reference sequence as R. Here S1 and S2 have the same size, and there is no restriction to R's size. Introduce a notation ordered_pair(i), which represents an ordered pair of elements at position i of S1 and S2. The two elements are ordered such that the first element is in S1 and the second in S2. For example if ordered_pair(2) is$(a_2, b_2)$, then $a_2$ is in S1 and $b_2$ is in S2; if we swap the elements, ordered_pair(2) will become $(b_2, a_2)$, that is, $b_2$ is in S1 and $a_2$ is in S2. An example of the swapping is shown in FIG. 6.

The optimization problem is as follows:

maximize (alignment_score(S1, R)+alignment_score (S2, R))

Where the maximization is over all possible ordered_pair (i),i=1, . . . , n and the alignment_score(S1/S2, R) is the alignment score between S1/S2 and R. The alignment score is calculated using a sequence alignment algorithm.

There are n ordered pairs for S1 and S2 with each pair having two different orders. The number of all possible combinations is therefore $2^n$. Using exhaustive enumeration of all combinations can always find the optimal solution. But obviously, for real-sized sequences, it is not practical. The present invention is not limited by the solution algorithm. In solving real-sized problem, we use heuristic search methods, which include local search, tabu search, simulated annealing and genetic algorithm. For simplicity and clarity, we will focus on the local search and tabu search algorithms in the following description.

Any heuristic search method that improves an objective function over a discrete search space can be used to solve the above optimization problem. In one embodiment, two heuristic search methods are employed. One method is a local search method. Another is a tabu search method. The two methods can be used either individually or in combination.

A heuristic search method is a tuple: (S, G, N, T, R), where S is the solution space over which the improvement of an objective function is sought, G is the gain function that maps every solution into a gain value, N is the neighborhood structure that defined the set of solutions that are in the neighborhood of the current solution, T is the transition that defines the legitimate search moves by which another solution is obtained from the current one, and R is the rule by which a transition from the current solution to another solution is accepted or rejected.

In terms of the tuple (S, G, N, T, R), the two methods to be described have (S, G, N, T) in common with R being different, where S is the $2^n$ possible combinations of ordered pairs states, G is the combined alignment score that is the objective function of the optimization problem, N is the all base assignments that can be obtained from the current base assignment by swapping one ordered pair, and T is a swap in one ordered pair. The R parameter is different between the two methods. The difference will be described as the methods are introduced.

In both methods, the alignment score is calculated by aligning a base sequence with a reference sequence. In some embodiments of the invention, the alignment method used is a dynamic programming algorithm, which will be described separately.

Local Search Method

The local search method iteratively improve the objective function by try to swap the element order in different ordered pair to see if the swap can improve the combined alignment score. The rule for accepting a swap is greedy, meaning that the method does not look ahead; it makes decision solely by the gain in a single step. Therefore a swap will be dropped unless it can improve the combined alignment score. The method's steps are listed below.

```
Step 1.   i =1; score* = alignment_score(S1, R) + alignment_score(S2, R);
          S1* = S1; S2* = S2.
Step 2.   Swap ordered_pair(i) score = alignment_score(S1, R) + alignment_score(S2, R).
          if (score > score*){ score* = score; S1* = S1; S2* = S2;}
          else      swap back ordered_pair(i).
Step 3.   i = i + 1; if i > n, stop; else go to step 2.
```

After the algorithm stops, the separated sequences are S1* and S2* and the best objective function value is score* that is the combined alignment score.

Tabu Search Method

The local search is simple and efficient. However, it is very subject to the trap of local optima. The reason is that it makes a move only if the move can strictly improve the objective function.

Tabu search is used to overcome the limitation of the local search. Tabu search is characterized by a so-called tabu list that is a list containing forbidden moves. A forbidden move is a search step that reverses a recent search step therefore brings the search back to where it started (therefore trapped). The size of the tabu list is defined as the maximum number of the forbidden moves allowed to be contained and is problem specific and determined empirically. Tabu search's rule for make a search step is to choose the best search step that is not on the tabu list. In so doing the trapping of local optima could be avoided.

In using the tabu search, the forbidden moves are defined as reversing recent swapped ordered pairs. After an ordered pair is swapped, it is put on the tabu list. Before making a new move, we first check with the tabu list to make sure we don't reverse a recent swap. It is worth noting that with the tabu list, the search steps (base pair swaps) that worsen the objective function are allowed, as long as the steps are the best ones that are not on the tabu list. Moving in a direction that worsens the objective function is how the search can escape from the trapping of local optima and move to the global optimum.

The following is the iterative steps for the tabu search.

```
Step 0. iteration = 0. best_score = big negative number.
Step 1. i =1; score* = alignment_score(S1, R) +
alignment_score(S2, R);
    S1* = S1; S2* = S2.
Step 2. Check the tabu List,
    if (i is not on the tabu list), Swap ordered_pair(i).
    else goto Step 3.
    score = alignment_score(S1, R) + alignment_score(S2, R).
    if (score > score*)
    {
        score* = score; put i onto the forbidden list.
        S1* = S1, S2* = S2.
    }
    else swap back ordered_pair(i).
Step 3. i = i + 1;
if( i > n)
{
    if(score* > best_score) {best_score = score*; best_S1 =
S1*; best_S2 = S2*;}
        iteration = iteration + 1;
        if (iteration > max_iteration), stop;
        else    go to Step 1.
    }
    else go to Step 2.
```

After the tabu search stops, the two improved base sequences are denoted by best_S1 and best_S2 and the best score best_score is the best-combined alignment score obtained.

Combined Methods

In some embodiments of this invention, the two search algorithms are combined. The local search algorithm is run first. It is efficient and typically can correct most of the wrong base assignment in the base sequences. The tabu search is then run using the result of the local search method as the staring point to make further improvement.

Alignment Algorithm

In certain embodiments of the invention, the alignment algorithm used in the heuristic search methods may be implemented as a dynamic programming method. Such methods compare a DNA sequence X to a reference DNA sequence R to find the mutations in X. With regard to the present invention, X and R are chosen from the same locus location and have about the same size. In such instances a global sequence alignment may be employed to align the two sequences over their entire length to find the mutations in X.

Global Sequence Alignment

In the following description, we consider aligning two sequences $X=\{x_1, \ldots, x_m\}$ and $R=\{r_1, \ldots, r_n\}$. An Edit Graph is a directed graph with mn nodes. The value (score) of a node is the length of the longest path from node($0, 0$) to that node. The Edit Graph can be represented by a score array $S=s_{i,j}, i=0, \ldots, m; j=0, \ldots, n$, where $s_{i,j}, i, j > 0$ is the largest alignment score (length of the corresponding longest path) of two subsequences $X_i=\{x_1, \ldots, x_i\}$ and $R_j=\{r_1, \ldots, r_j\}$, $s_{0,j}$ and $s_{i,0}$ are the gap penalties for the beginning gaps of an alignment between R and S.

The global sequence alignment problem is to find the longest path from node($0, 0$) to node($m, n$) in the Edit Graph. The length of the path is $s_{m,n}$ in S.

Gap Penalty

Deletions and insertions in aligned sequences are represented by gaps. The penalty for a gap of length L is defined as $-(\rho+\sigma L)$, where $\rho>0$ is gap initiation penalty and $\sigma>0$ is the gap extension penalty for a gap with size being equal to one.

Dynamic Programming

To calculate $s_{m,n}$ in array S, we use the following dynamic programming recursive step.

$$\Downarrow s_{i,j} = \max \begin{cases} \Downarrow s_{i-1,j} - \sigma \\ s_{i-1,j} - (\rho + \sigma) \end{cases}$$

$$\Rightarrow s_{i,j} = \max \begin{cases} \Rightarrow s_{i,j-1} - \sigma \\ s_{i,j-1} - (\rho + \sigma) \end{cases}$$

$$s_{i,j} = \max \begin{cases} s_{i-1,j-1} + \delta(x_i, r_j) \\ \Downarrow s_{i,j} \\ \Rightarrow s_{i,j} \end{cases}$$

$$s_{i,0} = -(\rho + i\sigma), \quad i > 0$$

$$s_{0,j} = -(\rho + j\sigma), \quad j > 0$$

$$s_{0,0} = 0$$

where $\Rightarrow s_{i,j}$ is the score for an alignment between $X_i$ and $R_j$ with $X_i$ ending with an insertion (a gap following $R_j$, which is in the last position of the alignment), $\Rightarrow s_{i,j}$ is the score for an alignment between $X_i$ and $R_j$ with $X_i$ ending with an deletion (a gap following $X_i$, which is in the last position of the alignment that follows $X_i$), and $\delta(x_i, r_j)$ is the similarity score between bases $x_i$ and $r_j$.

Here is an explanation about the gap penalty in the above recursive formula. In the Edit Graph, there are three ways to reach a node. Assume that the node is (i, j). It can be reached from (i-1, j-1), (i-1, j) or (i, j-1).

For the case when node (i,j) is reached from (i-1, j-1), there is no gap penalty involved. In the case where node (i,j) is reached from (i-1, j), we must look at how (i-1, j) is reached. If (i-1, j) is reached from (i-2, j), the gap is already opened at (i-2, j) or earlier, moving from (i-1, j) to (i, j) only incurs gap extension penalty. In the case that (i-1, j) is not reached from (i-2, j), we know that the gap is initiated at (i-1, j). As a result, moving from (i-1, j) to (i, j) incurs both the gap extension penalty and gap initiation penalty. In the case where (i,j) is reached from (i, j-1), the similar situation is analogous to reaching (i,j) from (i-1, j).

Mutation Identification (Mutation ID Module 118)

After applying the improvement methods to the two base sequences, the incorrect base assignments due to base insertion or deletion are resolved. The genetic mutations in the base sequences are then identified by aligning each of the sequences with the reference sequence using the alignment method described above.

Haplotyping (Haplotyping Resolution Module 122)

As mentioned previously, the base assignment could be incorrect due to two types of mutations: (1) base substitution and (2) base insertion/deletion. The incorrect base assignments due to base insertion/deletion are resolved using the heuristic search methods described above. The correction of incorrect base assignment due to base substitution is dealt with using haplotyping methods as is described below.

The purpose of haplotyping is to infer haplotype pairs from phase unknown genotype data. The knowledge of haplotypes is especially helpful in the association study and linkage disequilibrium analysis for diploid population. Two approaches are commonly used for haplotyping (1) maximum resolution methods (Clark, 1990; Gusfield, 2000) and (2) the EM algorithm (Excoffier and Slatkin, 1995).

A haplotyping method is used to derive the haplotypes from the gametic phase unknown genotypes that are represented by the base sequences resulted from applying the heuristic search methods described above. Note that after applying the heuristic search methods to align the base sequences with the reference sequence, incorrect base assignments caused by base insertion/deletion are corrected. Therefore most bases in the corresponding positions in the two base sequences are the same. If two bases in the corresponding positions are not the same in the base sequences, the difference is considered caused by base substitution, (i.e., genetic mutations are considered to exist at the positions). The EM algorithms' goal is to find the most likely haplotypes given a plurality of pairs of the base sequences with each having a plurality of such genetic mutations (ie., resolve the base assignments in each pair of base sequences where the ambiguity of base assignments is caused by base substitutions).

In applying a haplotyping method, a plurality of pairs of base sequences is obtained by first applying the heuristic search methods on a plurality of diploid DNA sequence signal. The bases are then removed from the base sequences if they are the same across all pairs of base sequences (i.e., there is no mutation occurred at those base positions). This removal reduces the base sequences to shorter sequences (denoted as reduced sequences) that only contain the base positions where genetic mutations occurred in at least one original base sequence. A haplotyping method is then applied to the reduced sequences.

In some embodiments of this invention, the haplotyping method is implemented as the EM algorithm described by Excoffier and Slatkin (see Excoffier and Slatkin, 1995). The algorithm is an iterative procedure with each iteration consisting of an expectation step and a maximization step to compute successive sets of haplotype frequencies. This procedure is straightforward to implement as a software application for those skilled in the art and need not be described in greater detail herein.

The heuristic search methods resolve the ambiguous/incorrect base assignment caused by the base insertion/deletion and the haplotyping methods resolve the ambiguous/incorrect base assignment caused by the base substitution. After applying the two sets of methods, all ambiguous/incorrect base assignments are resolved (i.e., the gametic phase is determined). The resulting pair of base sequences are therefore the two parental DNA alleles, also known as haploid alleles, for the individual.

Likelihood Score (Mutation Likelihood Score Module 120)

The likelihood score for an identified mutation is determined by the average quality score of the bases in the region surrounding the mutation. Assuming a mutation occurs at position p in a base sequence, term radius (in number of bases) is used to define the size of the region surrounding p. The surrounding regions for deletion, insertion and substitution are defined as follows:

For a deletion mutation occurring at position p in a base sequence, the surrounding region is defined as (p−radius, p+radius).

For an insertion mutation occurring at position p, the surrounding region is defined as (p−radius, p+i+radius), where i is the size (number of bases) of the insertion.

For a substitution mutation occurring at position p, the surrounding region is defined as (p−radius, p+s+radius), where s is the size (number of bases) of the substitution.

The likelihood score assigned to a mutation is the average value of the base-call quality scores in the mutation's surrounding region in the sequence.

The quality likelihood scores assigned to base substitution mutations may be affected by the noise in the diploid DNA sequence signal data. In some embodiments of the present invention, a noisy data handling method is included to minimize the negative impact of the noise. The present invention is not limited by the algorithm used to handle noisy data, but one such embodiment works as follows.

For each substitution, calculate the average noise level in its neighborhood. The neighborhood size is adjustable (e.g., 6 bases on each side of the mutation in the base sequence). The noise level is the average value of the base amplitude that is greater than zero and below a threshold (e.g., use the threshold value 20% of the average amplitude) in the neighborhood of the substitution.

For each substitution, calculate the ratio of the substitution's peak amplitude to the average noise level in the substitution's neighborhood. Denote the ratio SNR, short for signal to noise ratio.

Find the largest SNR in all substitutions for each of the base sequences.

Adjust the likelihood score of each substitution by multiply the likelihood score obtained by the ratio of SNR to the largest SNR in each of the base sequences.

Note that if the noise is more pronounced in a segment of the sequence, the value of the SNR will be low; the likelihood score for a substitution will also be low in that segment.

Methylation Analysis (Methylation Pattern ID Module 126)

Figure 3:
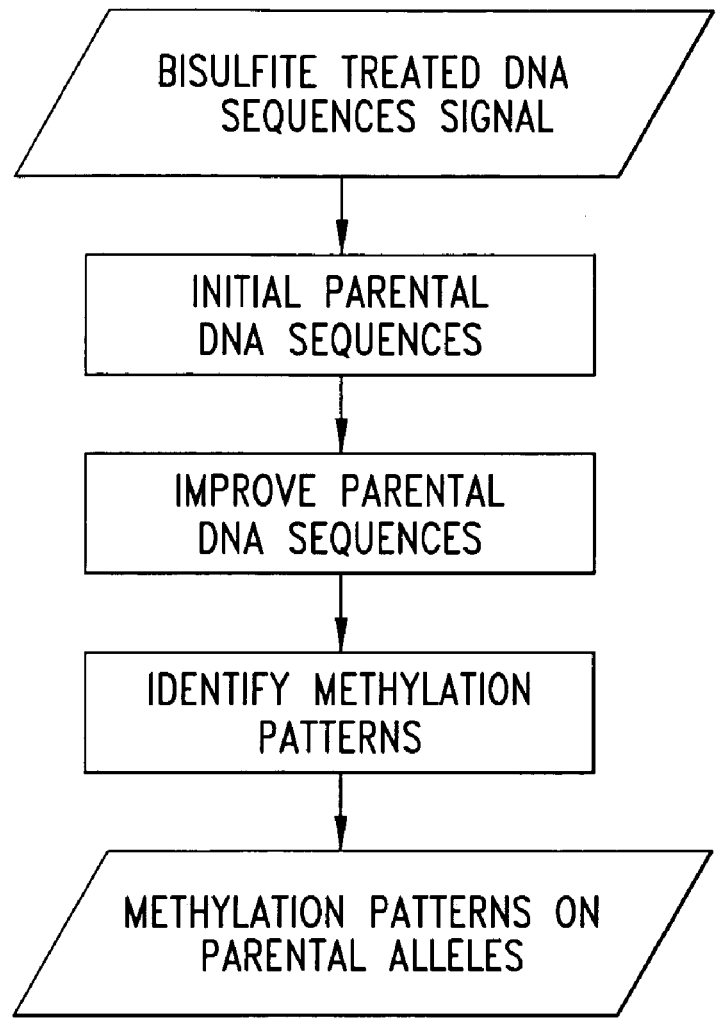
FIG. 3 illustrates one embodiment of an algorithm that enables the identification of methylation patterns from bisulfite-treated DNA sequence signals.

The entire process for the identification of methylation patterns includes the following steps: (1) selective deamination of cytosine to uracil, (2) PCR amplification converts all uracils into thymines, and (3) after the PCR, the methylation patterns can be identified by a comparison of the PCR amplified sequence and the original sequence. The first two steps are well known for those skilled in the art, therefore are not described herein. This invention focuses only on the methods for step 3 of the process. Step 3 is referred to as the methylation identification process hereafter. The steps for finding the methylation patterns are shown in FIG. 3.

In the following description, it is assumed that the bisulfite treatment and PCR amplification are completed. As a result, a methylated cytosine that is followed by a guanine in the 5' to 3' direction (CpG) remains a cytosine and unmethylated cytosines are converted to thymine in the bisulfite treated diploid DNA sequence signal.

In some embodiments of the present invention, the methylation identification process involves the following steps: (1) obtaining two initial bisulfite treated base sequences from the bisulfite treated diploid DNA sequence signal, (2) deriving two bisulfite treated parental DNA alleles from the two bisulfite treated initial base sequences, and (3) identifying methylation patterns in bisulfite treated parental DNA alleles by comparing them with the two original (untreated) parental DNA alleles. In all the three steps, the original parental DNA alleles are used as references for alignment. Therefore, before the methylation identification process, the parental DNA alleles need to be obtained using the methods described herein previously. The three steps are described below. In the following description, the two words "bisulfite treated" will be written as BT for simplicity. When the phrase "parental DNA alleles" appears without "BT" in front of them, it are refers to the original (untreated by bisulfite) sequences. The original sequences are used for aligning/comparing with "BT" sequences.

Initial Parental DNA Sequences

The method for obtaining the two initial BT base sequences from the BT diploid DNA sequence signal starts from the BT diploid DNA sequence signal. The method is the same as that used for obtaining the initial base sequences for parental DNA alleles. The result of the method is two initial BT base sequences. The two such obtained sequences typically contain wrong base assignments that are to be corrected in the next step.

Improve Parental DNA Sequences

Deriving two BT parental DNA alleles from the two BT initial base sequences involves iteratively improving the BT initial base sequences by base swapping between the BT initial base sequences to move the bases to their respective allele where they belong. The methods used are similar to those used for obtaining the parental DNA alleles. However, there is a difference between the two sets of methods. There is one reference sequence for the parental DNA alleles, both artificial parental DNA alleles are aligned with the reference sequence. In contrast, there are two reference sequences for deriving BT parental DNA alleles, each being one of the parental DNA alleles that are not treated by bisulfite. The result of the iterative improvement procedure is two BT parental DNA alleles with wrong base assignment corrected. More specifically, the iterative improvement procedure has the following objective function:

maximize combined_score=(alignment_score(S1, R1)+alignment_score(S2, R2))

where S1/S2 is one of the BT initial base sequences S1 and S2, R1/R2 is one of the original parental alleles R1 and R2, the maximization is over all possible ordered_pair(i), i=1, . . . , n, (as defined previously) the alignment_score (S1/S2, R1/R2) is the alignment score between S1/S2 and R1/R2 calculated using the dynamic programming algorithm.

The improvement procedure for methylation identification process is similar to the procedure for deriving the two original parental DNA alleles, which has been detailed in previous description. Because of the similarity, the procedure is only described briefly below. More details can be found in the description for obtaining the parental DNA alleles.

In an embodiment of this invention, the improvement procedure iteratively takes the following steps:

1) In the original parental DNA alleles, keep cytosines' labels if they are in the positions that are followed by a guanine in 5' to 3' direction (CpG) and re-label the cytosines in other positions as thymine. The re-labeled original parental DNA alleles are used as reference sequences and are referred as reference sequences.

2) Obtain a combined_score that is the sum of two alignment_scores with each being the alignment score of a BT initial base sequence and a reference sequence.

3) Tentatively update the BT initial base sequences by swapping the bases in position i of the two BT initial base sequences, where the two bases in position i is ordered_pair (i) that is defined previously. Multiple such tentative update can be made over different positions (e.g., swapping different ordered_pair(i)) and their results are recorded.

4) Compare the combined_score before and after said tentative updates, and commit a tentative update if it meets the criteria used by the search method, otherwise discard the tentative updates.

5) The iterative procedure terminates when the combined_score cannot be improved any further, otherwise repeat steps (2) to (5).

The above iterative procedure provides two results: the BT parental DNA alleles and the association of a BT parental DNA allele with its original parental DNA sequence. The next step is identifying the methylation patterns on the alleles.

Identifying Methylation Patterns

Note that the iterative procedure has established the association of a BT parental DNA allele with its original parental DNA allele. Based on the fact that the methylated cytosine remains cytosine in the BT parental DNA alleles, a methylated cytosine can be identified by comparing each cytosine in the 5' to 3' direction CpG dinucleotide in a BT parental DNA allele with the corresponding base in the associated original parental DNA sequence. If a cytosine remains cytosine in the BT parental DNA allele, it is methylated. Otherwise it is not methylated. The methylation pattern is obtained by identifying all methylated positions in parental DNA alleles.

Thus, a convenient apparatus and method are provided to identify haplotype from diploid DNA sequence signal data and to identify mutation patterns in the DNA. The operation of the apparatus and method can be extended to identify methylation patterns in diploid DNA sequence signal data.

All of the above U.S. patents, U.S. patent application publications, U.S. patent applications, foreign patents, foreign patent applications and non-patent publications referred to in this specification and/or listed in the Application Data Sheet, including but not limited to Andrew G. Clark, "Inference of Haplotypes from PCR-amplified Sample of Diploid Populations", Mol. Biol. Evol. 7(2): 111–122, 1990, Laurent Excoffier & Montgomery Slatkin, "Maximumlikelihood Estimation of Molecular Haplotype Frequencies in a Diploid Population", Mol. Biol. Evol. 12(5):921–927, 1995, Dan Gusfield, "A Practical Algorithm for Optimal Inference of Haplotypes from Diploid Populations", ISMB 2000 Proceedings, Eighth International Conference on Intelligent Systems for Molecular Biology, AAAI Press, 183–189, Ewing B, Hillier L, Wendl M C, Green P, Base-Calling of Automated Sequencer Traces Using Phred. I. Accuracy Assessment, Genome Res, Mar, 8(3):175–85, 1998, and Ewing B, Green P, Base-Calling of Automated Sequencer Traces Using Phred. II. Error Probabilities, Genome Res, Mar, 8(3):186–94, 1998, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for deriving two haploid DNA sequences from a diploid DNA sequence signal comprising:
   obtaining two initial base sequences from the diploid DNA sequence signal;
   determining alignments of each of the two initial base sequences with a reference DNA sequence; and
   deriving two haploid DNA sequences from the alignments.

2. The method of claim 1 wherein the diploid DNA sequence signal originates from an individual and is a combination of parental DNA sequence alleles each of which is inherited from one of the individual's parents wherein obtaining two initial base sequences comprises obtaining two initial base sequences from the parental DNA sequence alleles.

3. The method of claim 1 wherein the derived haploid DNA sequences are each a phase-unknown combination of DNA sequence alleles inherited from an individual's parents.

4. The method of claim 1, further comprising comparing each of the haploid DNA sequences relative to the reference sequence to identify polymorphisms.

5. The method of claim 4 wherein the polymorphisms comprise at least one substitution, insertion or deletion in at least one of the haploid DNA sequences.

6. The method of claim 4 wherein identifying the polymorphisms comprises aligning each of the haploid DNA sequences with the reference sequence using a dynamic programming method.

7. The method of claim 1 wherein obtaining, determining and deriving are applied across a plurality of diploid DNA sequence signals.

8. The method of claim 7, further comprising deriving DNA sequence haplotypes from the derived plurality of haploid sequences.

9. The method of claim 8 wherein deriving DNA sequence haplotypes comprises determining haplotypes from a plurality of pairs of gametic phase-unknown parental alleles to thereby determine actual parental DNA alleles.

10. The method of claim 9 wherein determining haplotypes comprises determining haplotypes using a selected one of an EM algorithm or a maximum resolution method.

11. The method of claim 1 wherein the diploid DNA sequence signal represents genomic DNA sequence signal data obtained from a sequencing operation conducted on an electrophoresis sequencing device wherein obtaining two initial base sequences comprises obtaining two initial base sequences from the genomic DNA sequence signal data obtained from the sequencing operation conducted on the electrophoresis sequencing device.

12. The method of claim 1 wherein the diploid DNA sequence signal is obtained by fluorescently labeling at least one nucleotide base in a mixture of DNA fragments of varying lengths wherein obtaining two initial base sequences comprises obtaining two initial base sequences from the fluorescently labeled at least one nucleotide base in the mixture of DNA fragments.

13. The method of claim 1 wherein the diploid DNA sequence signal comprises at least two multiplexed signals where each of the multiplexed signals represents a signal contribution arising from a single parental haplotype wherein obtaining two initial base sequences comprises obtaining two initial base sequences from the at least two multiplexed signals.

14. The method of claim 1 wherein deriving two haploid DNA sequences comprises improving the initial base sequences using at least one heuristic search method that improves an objective function over a discrete search space.

15. The method of claim 14 wherein the heuristic search method comprises a selected one of a local search method, a tabu search method, a simulated annealing algorithm, and a genetic algorithm.

16. The method of claim 14 wherein the objective function for the heuristic search methods is a combined alignment score that is a sum of two alignment scores with each score obtained from aligning one of the initial base sequences with the reference DNA sequence.

17. The method of claim 1 wherein deriving two haploid DNA sequences comprises improving the initial base sequences using at least one application of a heuristic search method taken together with a dynamic programming method for sequence alignment that transforms the initial base sequences to derive the two haploid DNA sequences.

18. The method of claim 17 wherein each application of the heuristic and dynamic programming methods comprises:
   obtaining a combined alignment score that is a sum of two alignment scores with each obtained from aligning one of the initial base sequences with the reference DNA sequence;
   making tentative updates on the initial base sequences;
   obtaining an updated combined alignment score that is the sum of two alignment scores with each obtained from aligning each tentatively updated initial base sequence with the reference DNA sequence;
   comparing the combined alignment score before and after the tentative updates;
   accepting the tentative updates if the tentative updates result in a combined alignment score that meets a criterion set for the heuristic search methods used, discarding the tentative updates otherwise; and
   evaluating whether the combined alignment score was improved by the application of methods.

19. A method for identifying the methylation patterns in a chemically-treated diploid DNA sequence signal relative to two reference haploid DNA sequences, comprising:
   deriving two chemically-treated haploid DNA sequences from the chemically-treated diploid DNA sequence signal;
   comparing the two reference haploid DNA sequences at nucleotide positions consisting of 5'-CpG-3' bases with the two chemically-treated haploid DNA sequences at the corresponding positions; and
   identifying the methylation pattern based on the comparison of the two reference haploid DNA sequences with the two chemically-treated haploid DNA sequences.

20. The method of claim 19 wherein the chemically-treated diploid DNA sequence signal is obtained from a sequencing operation conducted on an electrophoresis sequencing device and deriving the two chemically-treated haploid DNA sequences comprises deriving two chemically-treated haploid DNA sequences from the DNA sequence signal obtained from the electrophoresis sequencing device.

21. The method of claim 19 wherein the chemically-treated diploid DNA sequence signal originates from sequencing of an individual's genomic DNA that has been chemically treated to convert all unmethylated cytosines into a non-cytosine base.

22. The method of claim 19 wherein the chemically-treated diploid DNA sequence signal originates from sequencing of an individual's genomic DNA that has been treated with bisulfite to convert all unmethylated cytosines into uracils, with the uracils being further converted to thymines by a DNA polymerase during a DNA amplification or DNA sequencing process and deriving two chemically-treated haploid DNA sequences from the chemically-treated diploid DNA sequence signal comprises deriving two bisulfite-treated haploid DNA sequences from the bisulfite-treated DNA sequence signal obtained from the individual's bisulfite-treated genomic DNA.

23. The method of claim 19 wherein the chemically-treated diploid DNA sequence signal originates from an individual and is a combination of chemically-treated parental DNA sequence alleles each of which is inherited from one of the individual's parents and deriving the two chemically-treated haploid DNA sequences comprises deriving two chemically-treated haploid DNA sequences from the DNA sequence signal obtained from the combination of chemically-treated parental DNA sequence alleles.

24. The method of claim 19 wherein the two reference haploid DNA sequences represent two haploid contributions to the genomic DNA of the same individual from which the chemically-treated diploid DNA sequence signal is derived and comparing the two reference haploid DNA sequences with the two chemically-treated haploid DNA sequences comprises comparing the two reference haploid DNA sequences representing two haploid contributions to the genomic DNA of the same individual with the two chemically-treated haploid DNA sequences.

25. The method of claim 19, further comprising deriving the two reference haploid DNA sequences, deriving the two reference haploid DNA sequences comprising:
  obtaining two initial base sequences from a diploid DNA sequence signal originating from the same individual as the chemically-treated diploid DNA signal;
  determining alignments of each of the two initial base sequences with a reference DNA sequence; and
  deriving two reference haploid DNA sequences from the alignments.

26. The method of claim 19 wherein deriving the two chemically-treated haploid DNA sequences comprises:
  obtaining two initial base sequences from the chemically-treated diploid DNA sequence signal;
  determining alignments of each of the two initial base sequences with a reference DNA sequence; and
  deriving two chemically-treated haploid DNA sequences from the alignments.

27. The method of claim 26 wherein deriving the two chemically-treated haploid DNA sequences comprises improving the initial base sequences using at least one application of a heuristic search method taken together with a dynamic programming method for sequence alignment that transforms the initial base sequences to derive the two chemically-treated haploid DNA sequences.

28. The method of claim 27 wherein the chemically-treated diploid DNA sequence signal is a bisulfite-treated diploid DNA sequence signal and the two chemically-treated haploid DNA sequences are bisulfite-treated haploid DNA sequences to convert all unmethylated cytosines into a non-cytosine base, deriving two bisulfite-treated haploid DNA sequences comprising:
  relabeling the two reference haploid DNA sequences by changing the cytosine not in the 5'-CpG-3' to thymine, and denoting the relabeled two sequences as relabeled reference sequences;
  obtaining a combined alignment score that is a sum of two alignment scores with each obtained from aligning one of the initial sequences with one of the relabeled reference sequences, respectively;
  making tentative updates on the initial base sequences;
  obtaining an updated combined alignment score that is a sum of two alignment scores with each obtained from aligning each tentatively updated initial base sequences with one of the relabeled reference sequences, respectively;
  comparing the combined alignment score before and after the tentative updates;
  accepting the tentative updates if the tentative updates result in a combined alignment score that meets a criterion set for the heuristic search methods used, discarding the tentative updates otherwise; and
  repeating the above steps until no improvement in the alignment score can be made.

29. The method of claim 19 wherein comparing the reference haploid DNA sequence and the chemically-treated haploid DNA sequence comprises aligning each of the reference haploid DNA sequences with one of the chemically-treated haploid DNA sequences.

30. The method of claim 19 wherein the chemically-treated diploid DNA sequence signal is a bisulfite-treated diploid DNA sequence signal and the two chemically-treated haploid DNA sequences are bisulfite-treated haploid DNA sequences to convert all unmethylated cytosines into a non-cytosine base, wherein identifying the methylation pattern comprises identifying all positions of the 5'-CpG-3' in the two reference haploid DNA sequences at which the cytosine has been replaced by a thymine at the corresponding position in either of the bisulfite-treated haploid DNA sequences.

31. The method of claim 19 wherein deriving, comparing and identifying are applied across a plurality of chemically-treated diploid DNA sequence signals and corresponding reference haploid DNA sequences and then followed by a determination of methylation haplotype patterns using a selected one of an EM algorithm or a maximum resolution method.

32. A computer-implemented method of assigning a likelihood score to each genetic mutation identified on DNA sequences, comprising:
  receiving signals representative of bases in the DNA sequences;
  calculating a quality score for each base in the DNA sequences; and
  assigning likelihood scores to each of the genetic mutations by calculating an average of the quality scores in a region surrounding the mutation.

33. The method of claim 32 wherein calculating the quality score for each base comprises calculating at least one of the following parameters: (1) a spacing parity that is a measure of the discrepancy among distances in a segment adjacent to the base in the diploid DNA sequence signal, and (2) an amplitude parity that is a measure of a discrepancy among amplitudes of signal peaks in the segment adjacent to the base in the diploid DNA sequence signal.

34. The method of claim 33 wherein calculating the quality score for each base further comprises obtaining the quality score by looking up a value in a quality score table using the spacing parity and the amplitude parity as inputs to the quality score table, the value corresponding to the spacing parity and the amplitude parity inputs being the quality score.

35. The method of claim 32 wherein assigning the likelihood score for each of the genetic mutations comprises assigning the likelihood score for each mutation identified as an average value of quality scores of bases in a segment surrounding each mutation.

36. The method of claim 32 wherein the region surrounding each mutation is a region centered at the mutation and including pre-determined number of bases on each side of the mutation.

37. A computer-readable medium that causes a computer to derive two haploid DNA sequences from a diploid DNA sequence signal, by performing the steps of:
obtaining two initial base sequences from the diploid DNA sequence signal;
determining alignments of each of the two initial base sequences with a reference DNA sequence; and
deriving two haploid DNA sequences from the alignments.

38. The computer-readable medium of claim 37 wherein the computer-readable media causing the computer to obtain the two initial base sequences causes the computer to perform the steps of:
filtering out small signal peaks in the diploid DNA sequence signal;
designating a remaining at most two signal peaks at each position as valid bases; and
assigning each of the valid bases to a position in one of the two initial base sequences.

39. The computer-readable medium of claim 37 wherein the computer-readable media causing the computer to derive two haploid DNA sequences causes the computer to perform the steps of improving the initial base sequences using at least one heuristic search method that improves an objective function over a discrete search space.

40. The computer-readable medium of claim 39 wherein the heuristic search method comprises a selected one of a local search method, a tabu search method, a simulated annealing algorithm, and a genetic algorithm.

41. The computer-readable medium of claim 39 wherein the objective function for the heuristic search methods is a combined alignment score that is a sum of two alignment scores with each score obtained from aligning one of the initial base sequences with the reference DNA sequence.

42. The computer-readable medium of claim 37 wherein the computer-readable medium causing the computer to derive two haploid DNA sequences causes the computer to perform the steps of improving the initial base sequences using at least one application of a heuristic search method taken together with a dynamic programming method for sequence alignment that transforms the initial base sequences to derive the two haploid DNA sequences.

43. The computer-readable medium of claim 42 wherein each application of the heuristic and dynamic programming methods computer-readable medium causing the computer to perform the steps of:
obtaining a combined alignment score that is a sum of two alignment scores with each obtained from aligning one of the initial base sequences with the reference DNA sequence;
making tentative updates on the initial base sequences;
obtaining an updated combined alignment score that is the sum of two alignment scores with each obtained from aligning each tentatively updated initial base sequence with the reference DNA sequence;
comparing the combined alignment score before and after the tentative updates;
accepting the tentative updates if the tentative updates result in a combined alignment score that meets a criterion set for the heuristic search methods used, discarding the tentative updates otherwise; and
evaluating whether the combined alignment score was improved by the application of methods.

44. A computer-readable medium that causes a computer to identify methylation patterns in a chemically-treated diploid DNA sequence signal relative to two reference haploid DNA sequences, by performing the steps of:
deriving two chemically-treated haploid DNA sequences from the chemically-treated DNA sequence signal;
comparing the two reference haploid DNA sequences at nucleotide positions consisting of 5'-CpG-3' bases with the two chemically-treated haploid DNA sequences at the corresponding positions; and
identifying the methylation pattern based on the comparison of the two reference haploid DNA sequences with the two chemically-treated haploid DNA sequences.

45. The computer-readable medium of claim 44 wherein the computer-readable medium causing the computer to derive the two chemically-treated haploid DNA sequences causes the computer to perform the steps of:
obtaining two initial base sequences from the chemically-treated diploid DNA sequence signal;
determining alignments of each of the two initial base sequences with a reference DNA sequence; and
deriving two chemically-treated haploid DNA sequences from the alignments.

46. The computer-readable medium of claim 45 wherein the computer-readable medium causing the computer to derive the two chemically-treated haploid DNA sequences comprises computer-readable medium causing the computer to improve the initial base sequences using at least one application of a heuristic search method taken together with a dynamic programming method for sequence alignment that transforms the initial base sequences to derive the two chemically-treated haploid DNA sequences.

47. The computer-readable medium of claim 46 wherein the chemically-treated diploid DNA sequence signal is a bisulfite-treated diploid DNA sequence signal and the two chemically-treated haploid DNA sequences are bisulfite-treated haploid DNA sequences to convert all unmethylated cytosines into a non-cytosine base, wherein the computer-readable medium causes the computer to derive the two bisulfite-treated haploid DNA sequences by causing the computer to perform the steps of:
relabeling the two reference haploid DNA sequences by changing the cytosine not in the 5'-CpG-3' to thymine, and denoting the relabeled two sequences as relabeled reference sequences;
obtaining a combined alignment score that is a sum of two alignment scores with each obtained from aligning one of the initial sequences with one of the relabeled reference sequences, respectively;
making tentative updates on the initial base sequences;
obtaining an updated combined alignment score that is a sum of two alignment scores with each obtained from aligning each tentatively updated initial base sequences with one of the relabeled reference sequences, respectively;

comparing the combined alignment score before and after the tentative updates;

accepting the tentative updates if the tentative updates result in a combined alignment score that meets a criterion set for the heuristic search methods used, discarding the tentative updates otherwise; and repeating the above steps until no improvement in the alignment score can be made.

48. The computer-readable medium of claim 44 wherein the computer-readable medium causing the computer to compare the reference haploid and chemically-treated haploid DNA sequence comprises computer-readable medium causing the computer to perform the steps of aligning each of the reference haploid DNA sequences with one of the chemically-treated haploid DNA sequences.

49. The computer-readable medium of claim 44 wherein the chemically-treated diploid DNA sequence signal is a bisulfite-treated diploid DNA sequence signal and the two chemically-treated haploid DNA sequences are bisulfite-treated haploid DNA sequences to convert all unmethylated cytosines into a non-cytosine base, wherein the computer readable medium causing the computer to identify the methylation pattern comprises computer-readable medium causing the computer to perform the steps of identifying the methylation pattern comprises identifying all positions of the 5'-CpG-3' in the two reference haploid DNA sequences at which the cytosine has been replaced by a thymine at the corresponding position in either of the bisulfite-treated haploid DNA sequences.

50. The computer-readable medium of claim 44 wherein the computer-readable medium causing the computer to perform the steps of deriving, comparing and identifying are applied across a plurality of chemically-treated diploid DNA sequence signals and corresponding reference haploid DNA sequences and then followed by computer-readable medium causing the computer to perform the steps of deriving methylation haplotypes.

51. An apparatus to derive two haploid DNA sequences comprising:

an input interface coupled to a sequencing device to receive a diploid DNA sequence signal; and a processor configured to:
determine two initial base sequences from the diploid DNA sequence signal;
to determine alignments of each of the two initial base sequences with a reference DNA sequence; and
to derive two haploid DNA sequences from the alignments.

52. The apparatus of claim 51 wherein the processor is configured to identify the polymorphisms by aligning each of the haploid DNA sequences with the reference sequence using a dynamic programming method.

53. The apparatus of claim 51 wherein the processor is configured to determine the two initial base sequences comprising:

filtering out small signal peaks in the diploid DNA sequence signal;

designating a remaining at most two signal peaks at each position as valid bases; and assigning each of the valid bases to a position in one of the two initial base sequences.

54. The apparatus of claim 51 wherein the processor is configured to derive the two haploid DNA sequences by improving the initial base sequences using at least one application of a heuristic search method taken together with a dynamic programming method for sequence alignment that transforms the initial base sequences to derive the two haploid DNA sequences.

55. An apparatus to identify the methylation patterns in a chemically-treated diploid DNA sequence signal relative to two reference haploid DNA sequences, comprising:

an input interface coupled to a sequencing device to receive the chemically-treated diploid DNA sequence signal; and a processor configured to:
derive two chemically-treated haploid DNA sequences from the chemically-treated DNA sequence signal;
compare the two reference haploid DNA sequences at nucleotide positions consisting of 5'-CpG-3' bases with the two chemically-treated haploid DNA sequences at the corresponding positions; and
identify the methylation pattern based on the comparison of the two reference haploid DNA sequences with the two chemically-treated haploid DNA sequences.

56. The apparatus of claim 55 wherein the two reference haploid DNA sequences represent two haploid contributions to the genomic DNA of the same individual from which the chemically-treated diploid DNA sequence signal is derived and the processor is configured to compare the two reference haploid DNA sequences with the two chemically-treated haploid DNA sequences by comparing the two reference haploid DNA sequences representing two haploid contributions to the genomic DNA of the same individual with the two chemically-treated haploid DNA sequences.

57. The apparatus of claim 55 wherein the processor is further configured to derive the two reference haploid DNA sequences by:

obtaining two initial base sequences from the diploid DNA sequence signal;
determining alignments of each of the two initial base sequences with a reference DNA sequence; and
deriving two reference haploid DNA sequences from the alignments.

58. The apparatus of claim 55 wherein the processor derives the two chemically-treated haploid DNA sequences by:

obtaining two initial base sequences from the chemically-treated diploid DNA sequence signal;
determining alignments of each of the two initial base sequences with a reference DNA sequence; and
deriving two chemically-treated haploid DNA sequences from the alignments.

59. The apparatus of claim 58 wherein the processor is configured to derive the two chemically-treated haploid DNA sequences by improving the initial base sequences through the use of at least one application of a heuristic search method taken together with a dynamic programming method for sequence alignment that transforms the initial base sequences to derive the two chemically-treated haploid DNA sequences.

60. The apparatus of claim 59 wherein the chemically-treated diploid DNA sequence signal is a bisulfite-treated diploid DNA sequence signal and the two chemically-treated haploid DNA sequences are bisulfite-treated haploid DNA sequences to convert all unmethylated cytosines into a non-cytosine base, and the processor is configured to derive two bisulfite-treated haploid DNA sequences by:

relabeling the two reference haploid DNA sequences by changing the cytosine not in the 5'-CpG-3' to thymine, and denoting the relabeled two sequences as relabeled reference sequences;

obtaining a combined alignment score that is a sum of two alignment scores with each obtained from aligning one of the initial sequences with one of the relabeled reference sequences, respectively;

making tentative updates on the initial base sequences;

obtaining an updated combined alignment score that is a sum of two alignment scores with each obtained from aligning each tentatively updated initial base sequence with one of the relabeled reference sequences, respectively;

comparing the combined alignment score before and after the tentative updates;

accepting the tentative updates if the tentative updates result in a combined alignment score that meets a criterion set for the heuristic search methods used, discarding the tentative updates otherwise; and repeating the above steps until no improvement in the alignment score can be made.

61. An apparatus for assigning a likelihood score to each genetic mutation identified on DNA sequences, comprising:

an input device to receive data indicative of DNA sequences; and a processor configured to:

calculate quality scores for each base in the DNA sequences; and assign likelihood scores to each of the genetic mutations by calculating an average of the quality scores in the neighborhood of the mutation.

62. The apparatus of claim 61 wherein the computer is configured to assign the quality score for each base by calculating at least one of the following parameters: (1) a spacing parity that is a measure of the discrepancy among distances in a segment adjacent to the base in the diploid DNA sequence signal, and (2) an amplitude parity that is a measure of a discrepancy among amplitudes of the signal peaks in the segment adjacent to the base in the diploid DNA sequence signal.

63. The apparatus of claim 62 wherein the processor is configured to assign the quality score for each base by looking up a value in a quality score table using the spacing parity and the amplitude parity as inputs to the quality score table, the value corresponding to the spacing parity and the amplitude parity inputs being the quality score.

64. The apparatus of claim 61 wherein the processor is configured to assign the likelihood score for each of the genetic mutations by assigning the likelihood score for each mutation identified as an average value of quality scores of bases in the segment surrounding each mutation.

65. The apparatus of claim 61 wherein the neighborhood of each mutation is a region centered at the mutation and including pre-determined number of bases on each side of the mutation.

* * * * *